United States Patent [19]

Ebner, Jr.

[11] Patent Number: 4,772,202

[45] Date of Patent: Sep. 20, 1988

[54] DENTAL APPLIANCE REMOVAL DEVICE

[76] Inventor: Emanuel C. Ebner, Jr., 67 Schaefer Cir., Hudson, N.H. 03051

[21] Appl. No.: 887,551

[22] Filed: Jul. 17, 1986

[51] Int. Cl.⁴ .............................................. A61C 3/08
[52] U.S. Cl. .................................................. 433/150
[58] Field of Search .............. 433/150, 152, 153, 154, 433/155, 156, 157, 161, 173, 174

[56] References Cited

U.S. PATENT DOCUMENTS

| 1,094,269 | 4/1914 | Taylor | 433/154 |
| 2,428,689 | 10/1947 | Sykes | 433/157 |
| 3,254,412 | 6/1966 | Armao | 322/151 |

FOREIGN PATENT DOCUMENTS 3417067 11/1967 Fed. Rep. of Germany ...... 433/151

OTHER PUBLICATIONS

"Review of Methods for Removing Cast Gold Restorations", JADA, vol. 99, Nov. 1979, pp. 840-847.

Primary Examiner—Robert Peshock
Attorney, Agent, or Firm—Hamilton, Brook, Smith & Reynolds

[57] ABSTRACT

Side walls of an appliance removal device are joined by a transverse member which separates two cavities. One cavity receives a wax like compound which is pressed over a dental appliance. Grooves and orifices are formed in the side walls of that cavity. Flanges extend from the side walls into the other cavity to receive an impulse force from a tool positioned in that cavity. A pin on the other cavity serves to lock the tool in place with 10 degrees of freedom. Flanges extend outwardly from the side walls.

24 Claims, 3 Drawing Sheets

DENTAL APPLIANCE REMOVAL DEVICE

DESCRIPTION

BACKGROUND

Generally when a tooth is broken off or missing a bridge can be applied to replace that tooth. Similarly, a crown can be formed over a partially damaged tooth. The bridge or crown which is often called an appliance is carefully formed by a dentist to match the existing teeth of the patient. The appliance is generally made of material such as gold substrate which gives the bridge or crown structural support. Coating the surface of the appliance is a hard material such as porcelain which gives the appliance the color of the patient's natural teeth. The substrate and the porcelain are biologically non-reactive to the body.

In order to fit the appliance to the broken tooth or adjacent teeth in the case of a missing tooth, the tooth or teeth must be trimmed to the gum line. The appliance is then fitted over the trimmed region thereby filling the gap resulting from the broken or missing tooth. The appliance is attached to the trimmed region by a cement such as zinc oxide.

A problem that often occurs is that a tooth under the bridge or crown must sometimes be repaired. To enable access to the underlying tooth, the appliance must be removed. To remove the appliance, an impulse force must be applied to the cement to break the bond without damaging the underlying tooth, the periodontal tissues, or the appliance. If the appliance is damaged or broken then a new bridge or crown must be formed to replace the original, thus, resulting in a very expensive procedure for the patient.

Several methods are used to date for removing the appliance when repair to the underlying tooth is needed. Many of these methods are recited in *Review of Methods for Removing Cast Gold Restorations* by Richard A. Olivia, DDS, JADA, Vol. 99, November 1979. One of these methods is to use a hook device such as a reverse mallet at the edge of the appliance and apply an impulse force. One problem with employing this method is that you can chip the porcelain coating and damage the appliance. Another problem is that you can put a bending moment into the underlying tooth, causing the tooth, which has been weakened as a result of the trimming, to break off, thus, causing obvious pain to the patient.

In the case of a permanently cemented bridge, the general operation procedure is to take a saw and split the side of the appliance along the marginal side and along the crown. Once a split has been made, a small wedge is used to split open the appliance. The problem with this procedure is that the entire bridge is ruined. Additionally, there is a risk that the saw may cut into the underlying tooth and that the shock force applied by the wedge to the appliance will cause damage to the weakened tooth.

Another method employed by dentists is the Richwil crown remover device which is a gum-like device. To use the device, the gum is heated and applied to patient by placing it on the appliance and having the patient bite down. The gum device forms around and sticks to the crown or bridge and the opposing teeth. The dentist then requests the patient to separate his jaws thereby breaking the bond. The problem with this method is that often times the patient cannot develop sufficient force to break the bond. Also, cements which are commonly used by dentists require an impulse force to break the bond i.e., a constantly applied force will not break the bond.

There is, therefore, a need to remove a crown or bridge from dental patients without causing damage to the appliance or trauma to the tooth.

DISCLOSURE OF THE INVENTION

The present invention relates to an apparatus which removes a dental appliance without damaging the appliance or causing trauma to a patient's tooth. The apparatus comprises a removal device which has a fitting region and a pulling region. The fitting region has a cavity where a pellet of wax or wax compound is placed for attaching the appliance to the device. Preferably, there are slots located on the inside walls of the device to provide shear points for the compound. It is also preferred that orifices are located in the side walls to allow the dentist to observe an even distribution of the wax or wax-like compound. The pulling region has inner flanges which extend into a cavity. A head portion of an impulse tool is inserted into this cavity and imparts an impulse force against the inner flanges of device. This force is transmitted to a bond holding the appliance.

While the present invention allows the head of the impulse tool to have enough flexibility within the cavity to apply an impulse force local to the area of the bond, it is preferred that the degree of flexibility does not extend beyond 10 degrees relative to a line of draw of crown or bridge on the long axis of the tooth. If a force is applied by the tool beyond these limitations then a harmful bending moment could be applied to the tooth. to, enable an impulse force to be imparted to one side of the device, it is preferred that outer flanges are provided.

To provide safety to the patient and the appliance, it is preferred that a pin means is mounted within the cavity of the pulling region to provide a locking means to keep the impulse tool connected to the removal device when the appliance breaks free from the tooth.

BRIEF DESCRIPTION OF THE DRAWINGS

The foregoing and other objects, features, and advantages of the invention will be apparent from the following more particular description of the preferred embodiments of the invention, as illustrated in the accompanying drawings in which like reference characters refer to the same parts throughout the different views. The drawings are not necessarily to scale, emphasis instead being placed upon illustrating the principles of the invention.

DESCRIPTION OF PREFERRED EMBODIMENTS

The present invention is an apparatus which removes a dental appliance without damaging the appliance or causing trauma to a patient's tooth. The apparatus consists of a removal device and a tool used for imparting an impulse force to the removal device.

Figure 1:
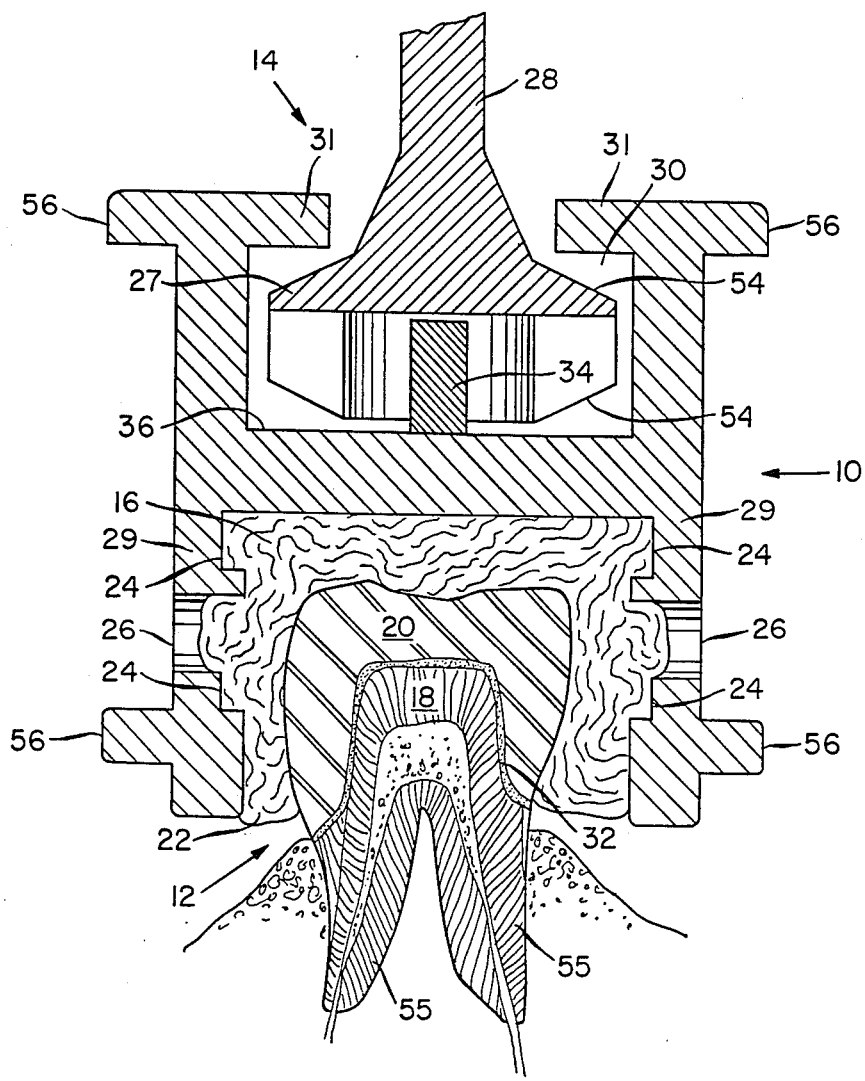
FIG. 1 is a cross sectional view of a removal device emboding the present invention.

A cross section of the removal device 10 is shown in FIG. 1. As shown, the device 10 has two regions, a fitting region 12 and a pulling region 14. The fitting region 12 has a cavity 16 which is mounted over a tooth 18 having a dental appliance 20. Between the fitting region 12 and the appliance 20 there is a wax or wax-like compound 22 which temporarily sticks to the appliance 20 and the device 10. Preferably, the compound 22 has shear strength when an impulse force is applied but otherwise acts like a fluid when a slow constant pressure is applied. Currently, there are several compounds on the market having these properties and are generally available to dentists. In order to increase the grip of the compound 22 within the fitting region 12, it is preferred that slots 24 are formed inside of the walls 29 of the fitting cavity 16.

A preferred way of mounting the removal device is to place a pellet of the compound 22 into the cavity 16 of the fitting region 12 before placing the removal device 10 on the appliance covering the patient's prepared tooth 18. For some compounds of wax-like material, the wax and device may be warmed before mounting to enhance the fluid characteristics of the compound. Once on the appliance, the dentist then requests that the patient apply a slow, constant pressure by biting down on the device 10 to allow the compound 22 to flow evenly around the appliance 20 and the cavity 16. To insure that the compound 22 has been evenly applied, it is preferred that there is at least one orifice 26 on each side wall 29 of the device adjacent to the fitting region 12. Preferably the size of the orifice 26 is small enough so that the device is not substantially weakened but large enough to allow the dentist to see if there has been a proper spreading of the compound 22 by observing the amount of compound 22 that comes through the orifice 26. An additional advantage of having orifices is that more shear points are provided. After the compound has been properly applied and the removal device 10 is attached to the appliance 20, a head portion 27 of an impulse tool assembly 28 is then slid into a cavity 30 of a pulling region 14, having inner flanges 31, from either the front or back of the removal device 10. The inner flanges 31 are used to receive the impulse force of the tool 28 and transmit the force to a bond 32 holding the appliance 20 to the tooth 18.

Figure 2:
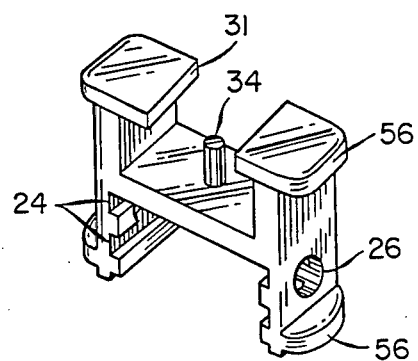
FIG. 2 is a perspective view of the removal device.

The dimensions of the removal device 10 such as length may vary depending on whether it is to be used to remove the appliance from one tooth or a row of teeth as in the case of the bridge work. Both embodiments are respectively shown in FIGS. 2 and 3. Similarly, different widths of the removal device are possible depending on whether it is to be used to remove a front tooth such as an eye tooth or a back tooth such as a molar.

Figure 3:
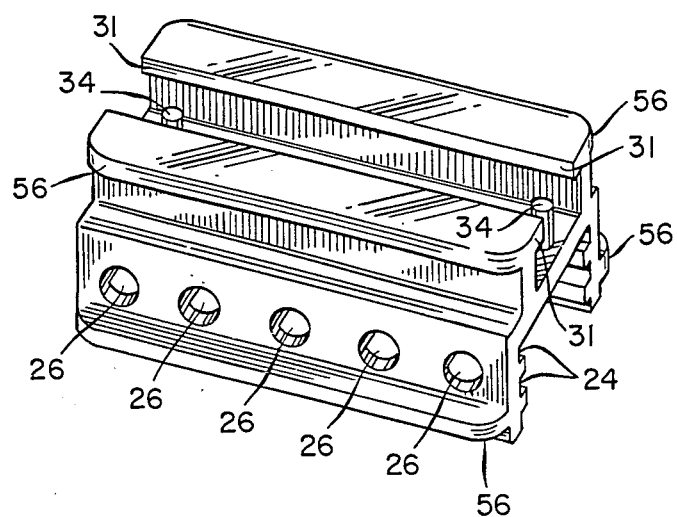
FIG. 3 is a perspective view of an alternative removal devise embodying the present invention.
Figure 5:
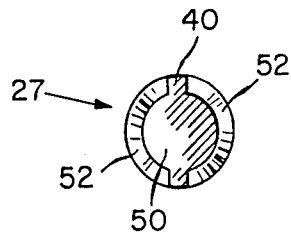
FIG. 5 is a view of the head portion of the impulse tool shown in FIG. 4.

In order to protect the patient as well as the appliance, the present invention provides for a safety feature which locks the impulse tool assembly 28 and the removal device 10 together when the bond 32 suddenly breaks free. As shown in FIG. 1, a pin 34 is fixed to a floor 36 of the cavity 30 in the pulling region 14. The tool is locked to the device by, first, sliding the head portion 27 of the tool 28 which has slots 40 (shown in FIG. 5) to allow the head 27 to pass over the pin 34 and, then, rotating the tool 28 about the pin so that the slots are adjacent to the side walls of cavity 30. When a long device such as that shown in FIG. 3 is used; it is preferred that two pins are located at the front and back of the device. When the head 27 of the impulse tool assembly 28 is slid over one of the pins 34 and turned relative to the pin's axis, the tool becomes locked in between the two pins, thereby achieving the safety feature already discussed.

Figure 4:
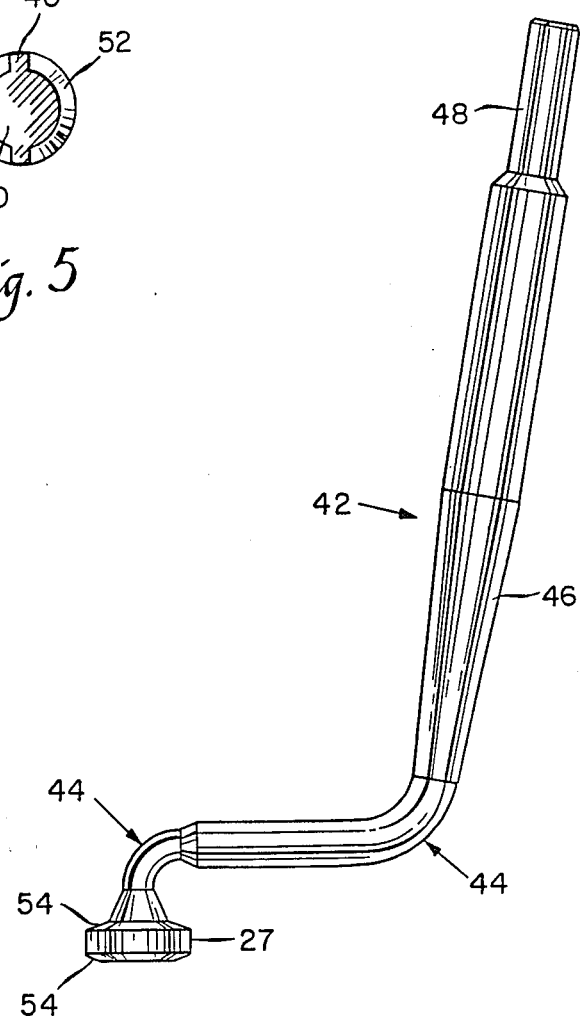
FIG. 4 is a side view of an impulse tool attachment used in conjunction with the removal device embodied in FIG. 1.

The impulse tool assembly 28 used in conjunction with the removal device 10 preferably consists of an impact tool (not shown) such as a reverse mallet and an attachment to the impulse tool used for a particular application of the removal device 10. For example, in FIG. 4 a side view of a preferred impulse tool attachment 42 is shown. Bends 44 in a handle region 46 of the attachment adjacent to the head region 27 allow the dentist to operate from the side of the patient's face while working on an appliance in the back portion of the mouth. Other attachments having various lengths and degrees of bends other than that shown, however, are possible for working in the other areas of the patient's mouth. At the end of the handle region 48, it is preferred that an attaching means such as threads are provided to allow this attachment to be easily fitted to the impulse tool. Impact tools embodying the present invention which do not employ interchangeable attachments are also possible.

Often times, during removal of the appliance, only a portion of the bond will break free, after an impulse force has been applied. Therefore, it is preferred that the head region 27 of the tool have a counter bore 50 leaving a wall portion 52 for containing the pin and tapered edges 54 to allow some freedom to redirect the impulse force within the pulling region 14. The degree of freedom, however, should be limited to 10 degrees from the line of draw of the crown on the long axis of the tooth. The long axis is defined as the length of the tooth from a root 55 to the appliance 20. This limitation insures that the impulse force does not create a harmful bending moment on the tooth.

In some instances, only an impulse force applied to one side of the appliance will break the appliance free from the tooth. For these cases it is preferred that the removal device have outside flanges 56. These flanges 56 allow standard tools such as a reverse mallet with a hook attachment to be used.

While the invention has been particularly shown and described with reference to preferred embodiments thereof, it will be understood by those skilled in the art that various changes in form and details may be made therein without departing from the spirit and scope of the invention, as defined by the appended claims. For example, other locking means such as a pin with a ball-point head and a tool with a key hole slot configuration is possible. Also, a pin or flange may be located on the side walls of the removal device to accomplish a locking device.

I claim:

1. A device for removing a dental appliance, the removal device comprising:
   a first side wall connected to a second side wall by a transverse member, the walls defining a first cavity therebetween to one side of the transverse member, the first cavity having inner flanges extending therein from the walls for receiving an impulse force from a tool positioned within the first cavity; and
   the walls defining a second cavity therebetween to a side of the transverse member opposite to the first cavity for fitting over the appliance, the device being adapted to receive a wax or wax-like compound in the second cavity and to be placed over the appliance with the wax or wax-like compound formed about the appliance and adapted to thereafter receive in the first cavity the tool to engage the inner flanges, the engaged tool being isolated from the compound in the second cavity for applying the impulse force to the flanges.

2. A removal device as claimed in claim 1, further comprising an outer flange located on the first and second side walls and directed away from the cavities.

3. A removal devices as claimed in claim 1, wherein the first and second side walls have at least one orifice in communication with the second cavity.

4. A removal device as claimed in claim 1, further comprising the wax or wax-like compount in the second cavity for attaching the appliance to the removal device.

5. A removal device as claimed in claim 4, wherein the first and second side walls have slots located within the second cavity to create shear points for the compound.

6. A removal device as claimed in claim 1, further comprising a tool assembly having a head portion which fits within the first cavity for applying an impulse force to the inner flanges.

7. A removal device as claimed in claim 6, further comprising a pin means mounted within the first cavity to provide a means for locking the tool assembly to the removal devise.

8. A removal device as claimed in claim 6, wherein the tool has a maximum of 10 degrees of freedom, within the first cavity, relative to a line of draw of a crown or bridge along the long axis of the tooth.

9. An apparatus for removing a dental appliance comprising:
a removal device having a first side wall connected to a second side wall to form a first cavity with inner flanges extending therein from the side walls, and a second cavity for fitting over the appliance;
a wax-like compound for insertion into the second cavity for attaching the appliance to the removal device; and
a tool which fits within the first cavity to engage the inner flanges after the appliance is attached to the removal device for applying an impulse force to the inner flanges.

10. An apparatus for removing a dental appliance as claimed in claim 9, further comprising an outer flange located on the first and second side walls and directed away from the cavities for receiving impulse forces to the side of the removal device.

11. An apparatus for removing a dental appliance as claimed in claim 9, wherein the first and second side walls have slots located within the second cavity to create shear points for the compound.

12. An apparatus for removing a dental appliance as claimed in claim 9, wherein the first and second side walls have at least one orifice in communication with the second cavity.

13. An apparatus for removing a dental appliance as claimed in claim 9, further comprising a pin means mounted within the first cavity to provide a means for locking the tool to the removal device.

14. An apparatus for removing a dental appliance as claimed in claim 9, wherein the tool has a maximum of 10 degrees of freedom, within the first cavity, relative to a vertical axis of the dental appliance.

15. A method of removing a dental appliance comprising the steps of:
filling a first cavity of a removal device with a wax-like compound, the compound capable of temporarily sticking to the appliance and transmitting an impulse force;
applying the removal device to the dental appliance; and
thereafter coupling a tool to the removal device for applying an impulse force to the removal device and through the wax-like compound such that the dental appliance is removed.

16. A method of removing a dental appliance as claimed in claim 15 further comprising the step of inserting a tool within a second cavity of the removal device for applying an impulse force and locking the tool to the removal device.

17. A method as claimed in claim 15 wherein the wax-like material is able to flow around the appliance.

18. A method of removing a dental appliance as claimed in claim 15 further comprising the step of inserting a tool within a second cavity of the removal device for applying an impulse force to the removal device.

19. Apparatus for removing a dental appliance comprising:
a removal device having an open-ended cavity formed between side walls joined by a transverse member, the cavity fitting over the appliance with the side walls on opposite sides of the appliance;
a wax-like joining material, which is able to flow around the appliance, set within the cavity for temporarily joining the removal device to the appliance while remaining fluid; and
impulse means on the removal device adapted to be engaged by a tool after the removal device is joined to the appliance for receiving an impulse force from the tool which is transmitted through the wax-like material to the appliance.

20. Apparatus as claimed in claim 19 wherein the removal device further comprises a second cavity to a side of the transverse member opposite to the open ended cavity, the second cavity being formed between side walls having inwardly directed flanges extending therefrom for receiving the impulse force.

21. Apparatus as claimed in claim 20 further comprising at least one outer flange directed away from the cavities.

22. Apparatus as claimed in claim 21 further comprising a pin extending into the second cavity from the transverse member to provide means for locking a tool within the second cavity for applying the impulse force.

23. Apparatus as claimed in claim 22 wherein the side walls forming the open ended cavity have slots therein within the cavity to create shear points for the joining material.

24. Apparatus as claimed in claim 23 wherein at least one side wall forming the open ended cavity has at least one orifice in communication with the cavity.

* * * * *